United States Patent
DeRosa et al.

(10) Patent No.: US 9,801,995 B2
(45) Date of Patent: Oct. 31, 2017

(54) COVER FOR HOUSING A SYRINGE, ASSEMBLY COMPRISING SUCH COVER, PEN-INJECTOR COMPRISING SUCH ASSEMBLY AND METHOD FOR FORMING A PEN-INJECTOR

(75) Inventors: Francesco DeRosa, Sollentuna (SE); Torbjorn Lindwall, Sollentuna (SE); Anna Sahlin, Sollentuna (SE); Rolf Skedelius, Gnesta (SE)

(73) Assignee: Pfizer Health AB, Stockholm (SE)

( * ) Notice: Subject to any disclaimer, the term of this patent is extended or adjusted under 35 U.S.C. 154(b) by 185 days.

(21) Appl. No.: 14/000,987

(22) PCT Filed: Mar. 14, 2012
(Under 37 CFR 1.47)

(86) PCT No.: PCT/IB2012/051200
§ 371 (c)(1),
(2), (4) Date: Jul. 29, 2014

(87) PCT Pub. No.: WO2012/127365
PCT Pub. Date: Sep. 27, 2012

(65) Prior Publication Data
US 2014/0378909 A1    Dec. 25, 2014

Related U.S. Application Data

(60) Provisional application No. 61/466,281, filed on Mar. 22, 2011.

(51) Int. Cl.
*A61M 5/00* (2006.01)
*A61M 5/28* (2006.01)
*A61M 5/31* (2006.01)
*A61M 5/315* (2006.01)

(52) U.S. Cl.
CPC ............ *A61M 5/002* (2013.01); *A61M 5/284* (2013.01); *A61M 5/3129* (2013.01); *A61M 5/3137* (2013.01); *A61M 5/31511* (2013.01); *A61M 2005/3139* (2013.01); *A61M 2207/00* (2013.01); *Y10T 29/49826* (2015.01)

(58) Field of Classification Search
CPC ................ A61M 5/008; A61M 5/3221; A61M 2005/3254
See application file for complete search history.

(56) References Cited

U.S. PATENT DOCUMENTS

| 4,430,079 A | 2/1984 | Thill et al. |
| 4,681,566 A * | 7/1987 | Fenton, Jr. .......... A61M 5/1454 128/DIG. 12 |
| 9,233,205 B2 * | 1/2016 | Renz ................... A61M 5/2033 |
| 2002/0050462 A1 | 5/2002 | Penney et al. |

FOREIGN PATENT DOCUMENTS

WO    2010069573    6/2010

* cited by examiner

Primary Examiner — Kevin C Sirmons
Assistant Examiner — Deanna K Hall
(74) Attorney, Agent, or Firm — Lisa A. Samuels

(57) ABSTRACT

The invention relates to a cover for housing a syringe, an assembly comprising such cover, a pen-injector comprising such assembly and a method for forming a pen-injector.

7 Claims, 4 Drawing Sheets

Figure 1:
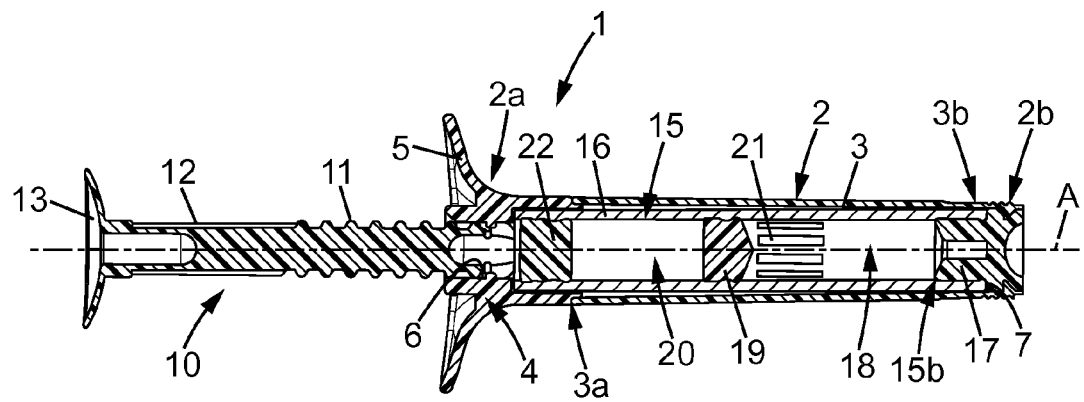

COVER FOR HOUSING A SYRINGE, ASSEMBLY COMPRISING SUCH COVER, PEN-INJECTOR COMPRISING SUCH ASSEMBLY AND METHOD FOR FORMING A PEN-INJECTOR

CROSS REFERENCE TO RELATED APPLICATIONS

This application claims priority to international application number PCT/IB2012/051200 filed on Mar. 14, 2012, which claims priority from U.S. Provisional Application Ser. No. 61/466,281, filed Mar. 22, 2011, all of which are incorporated in their entireties for all purposes.

The invention relates to a cover for housing a syringe, an assembly comprising such cover, a pen-injector comprising such assembly and a method for forming a pen-injector.

The invention finds a particular application in a pen-injector used as an injection device to ease the delivery of a determined dose of product, especially a therapeutic or pharmaceutical product, to a patient, most of time by the patient himself.

A known pen-injector, in particular an auto-injector, comprises a syringe and a cover for housing the syringe. The cover comprises a shell extending along a longitudinal axis and adapted to accommodate the syringe so that at least a part of a needle of the syringe extends from the shell. The cover also comprises an actuator moveably mounted on the shell and arranged to actuate the syringe. In the known pen-injector, the shell has a cavity extending along the longitudinal axis between a proximal end and an opened distal end through which the syringe is inserted along the longitudinal axis into the cavity.

However, the known pen-injector is complex to handle, especially regarding the mounting and the positioning of the syringe with respect to the shell. Thus, the known pen-injector does not offer a convenient use to the patient. Besides, the known pen-injector can hardly be adapted to different kinds of syringe.

The invention aims to solve the above mentioned problems.

To this end, according to a first aspect, the invention provides for a cover for housing a syringe, said syringe comprising a body extending along an axis between proximal and distal ends and adapted to contain a product to be injected, a finger grip protruding outwardly from the body, a piston rod coaxially mounted in the body so as to slide along the axis of the body, and a needle mounted on the distal end of the body, said cover comprising:
a shell extending along a longitudinal axis between proximal and distal ends, said shell being adapted to accommodate the body, the finger grip and the piston rod of the syringe so that at least a part of the needle of the syringe extends through the distal end of the shell,
an actuator moveably mounted on the shell and arranged to actuate the piston rod of the syringe when the syringe is placed in the shell,
wherein the shell is provided with a holding member adapted to hold the finger grip of the syringe, and
wherein the shell comprises a base and a lid, said base including a cavity extending along the longitudinal axis of the shell and adapted to receive the syringe with the axis of the body parallel to the longitudinal axis of the shell, said lid being movable with respect to the base between an opened position in which the shell presents a lateral access to the cavity to allow insertion or removal of the syringe, and a closed position.

Hence, the shell made of two moveable parts makes it easier to handle the cover. The lateral access to the cavity in which the syringe is placed provides for a wild opening transverse to the longitudinal axis and that eases the mounting and the right positioning of the syringe in the cover. Besides, the base simplifies the ability to adapt the cavity and the lateral access to different kinds of syringe.

In particular, the lateral access opens transversally with respect to the longitudinal axis of the shell in the opened position of the lid.

In an embodiment, the base and the lid are articulated with respect to each other. The lid may be pivotally mounted on the base about a pivot axis between the opened position in which said lid is angularly spaced from the base, and the closed position in which said lid covers the cavity. In particular, the lid may be mounted on the base at the distal end of the shell and the pivot axis extends transversally with respect to the longitudinal axis of the shell.

Besides, the holding member may comprise two slots opened transversally with respect to the longitudinal axis of the shell and extending on either sides of the cavity, said slots being designed to accommodate two opposite portions of the finger grip projecting transversally from the body.

The base may have a hoop at the proximal end of the shell, said hoop being arranged coaxially to the longitudinal axis of the shell and delimiting an opening in which the actuator is mounted so as to slide along the longitudinal axis of the shell. The actuator may have an outer surface and the base may comprise a friction member resiliently biased against the outer surface of the actuator.

To improve the grasping and the stability of the cover, the shell may have two opposite outer surfaces which are substantially flat.

According to a second aspect, the invention proposes an assembly comprising a cover as previously defined, and a syringe, said syringe comprising:
a body extending along an axis between proximal and distal ends and adapted to contain a product to be injected,
a finger grip protruding outwardly from the body,
a piston rod coaxially mounted in the body so as to slide along the axis of the body, and
a needle mounted on the distal end of the body.

The finger grip of the syringe may comprise two opposite portions projecting transversally from the body, the holding member comprising two slots opened transversally with respect to the longitudinal axis of the shell and extending on either sides of the cavity.

The piston rod may be moveable with respect to the body along an injection stroke, and the actuator may be coaxially mounted on the proximal end of the shell so as to slide along the longitudinal axis of the shell, the actuator comprising an actuating surface arranged within the cavity of the base so as to move the piston rod when the syringe is placed in the shell and the actuator is pressed towards the distal end of the shell, the actuator being moveable with respect to the shell between an extended position and a depressed position over a distance greater than or equal to the injection stroke of the piston rod.

The syringe may have an initial state in which a proximal end of the piston rod is arranged at a first distance from the finger grip, and a ready-to-be-used state in which the proximal end of the piston rod is arranged at a second distance from the finger grip, the second distance being less than the first distance, and the actuating surface of the actuator in the extended position may be arranged at a distance from the holding member corresponding to the second distance of the syringe in the ready-to-be-used state.

According to a third aspect, the invention proposes a pen-injector comprising an assembly as previously defined, wherein the shell accommodates the body, the finger grip and the piston rod of the syringe so that at least a part of the needle of the syringe extends through the distal end of the shell, the holding member of the shell holding the finger grip of the syringe, the cavity of the base receiving the syringe with the axis of the body parallel to the longitudinal axis of the shell, the lid being in the closed position.

According to a fourth aspect, the invention proposes a method for forming a pen-injector comprising the steps of:
  providing an assembly as previously defined,
  placing the lid of the shell in the opened position,
  placing the syringe within the cavity of the base of the shell through the lateral access,
  moving the lid to the closed position, the shell accommodating the body, the finger grip and the piston rod of the syringe so that at least a part of the needle of the syringe extends through the distal end of the shell, the holding member of the shell holding the finger grip of the syringe, the cavity of the base receiving the syringe with the axis of the body parallel to the longitudinal axis of the shell.

In an embodiment, the step of providing the assembly may comprise providing the lateral access that opens transversally with respect to the longitudinal axis of the shell in the opened position of the lid, and the step of placing the syringe within the cavity of the base may comprise moving the syringe transversally with respect to the longitudinal axis of the shell.

Besides, the step of providing the assembly may comprise:
  providing the syringe having an initial state in which a proximal end of the piston rod is arranged at a first distance from the finger grip, and a ready-to-be-used state in which the proximal end of the piston rod is arranged at a second distance from the finger grip, the second distance being less than the first distance, the piston rod being moveable with respect to the body along an injection stroke,
  providing the cover with the actuator coaxially mounted on the proximal end of the shell so as to slide along the longitudinal axis of the shell, the actuator comprising an actuating surface arranged within the cavity of the base so as to move the piston rod when the syringe is placed in the shell and the actuator is pressed towards the distal end of the shell, the actuator being moveable with respect to the shell between an extended position and a depressed position over a distance greater than or equal to the injection stroke of the piston rod, the actuating surface of the actuator in the extended position being arranged at a distance from the holding member corresponding to the second distance of the syringe in the ready-to-be-used state,
  said method further comprising, prior to the step of placing the syringe within the cavity of the base, the step of moving the syringe from the initial state to the ready-to-be-used state.

Figure 2:
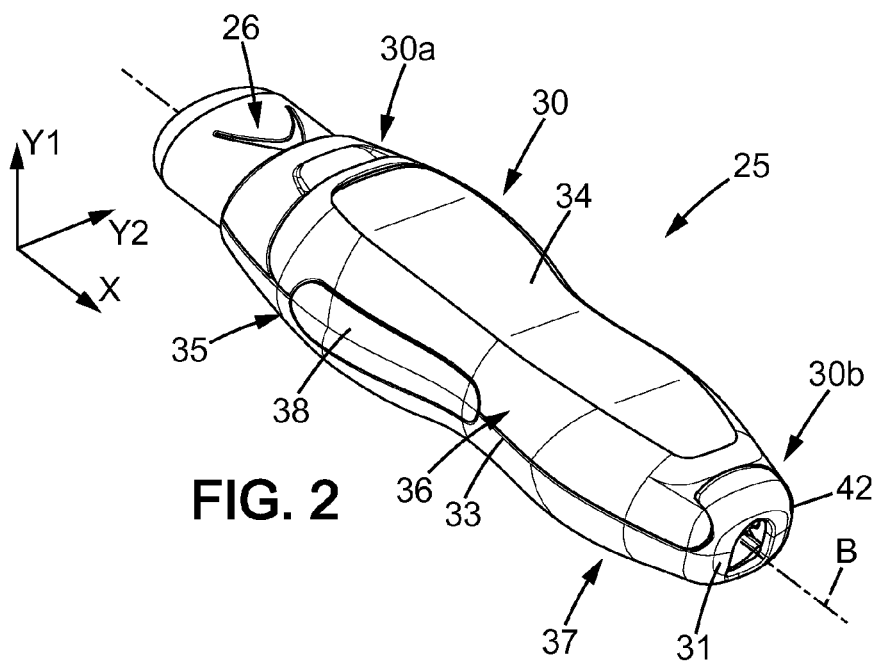
Figure 3:
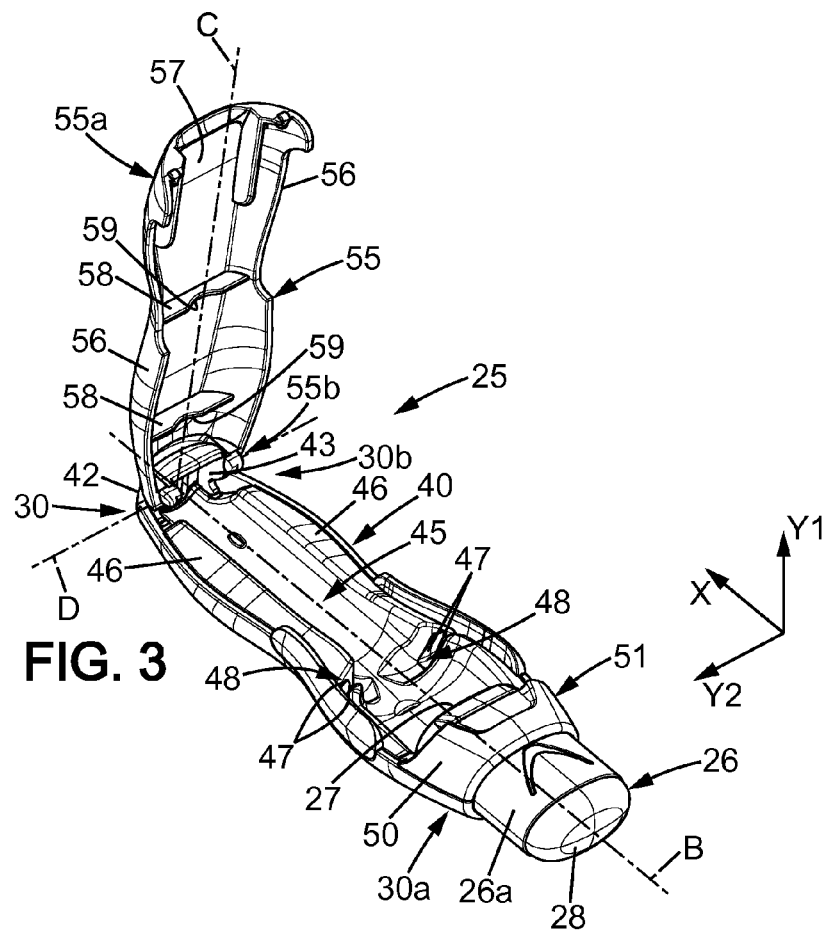
Figure 4:
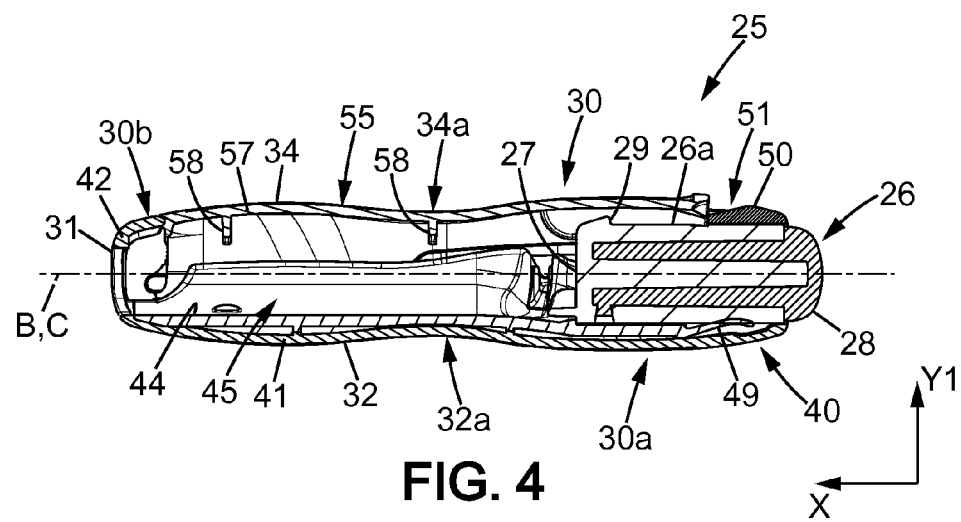
Figure 5:
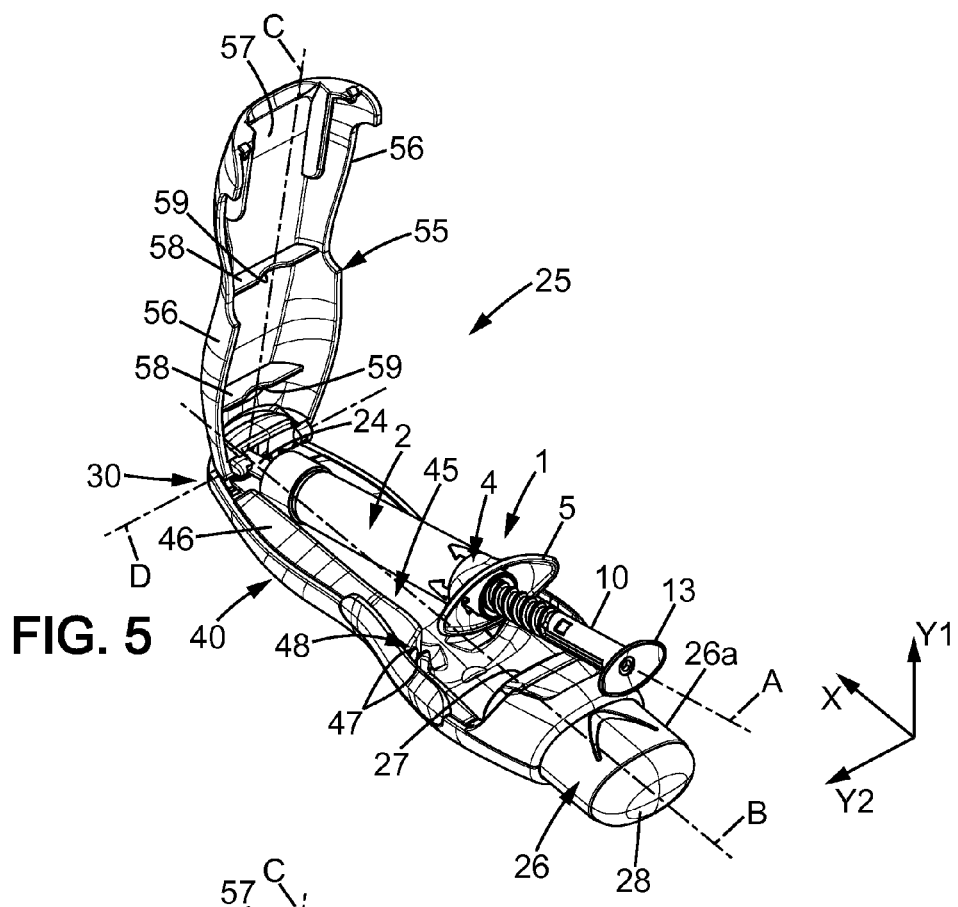
Figure 6:
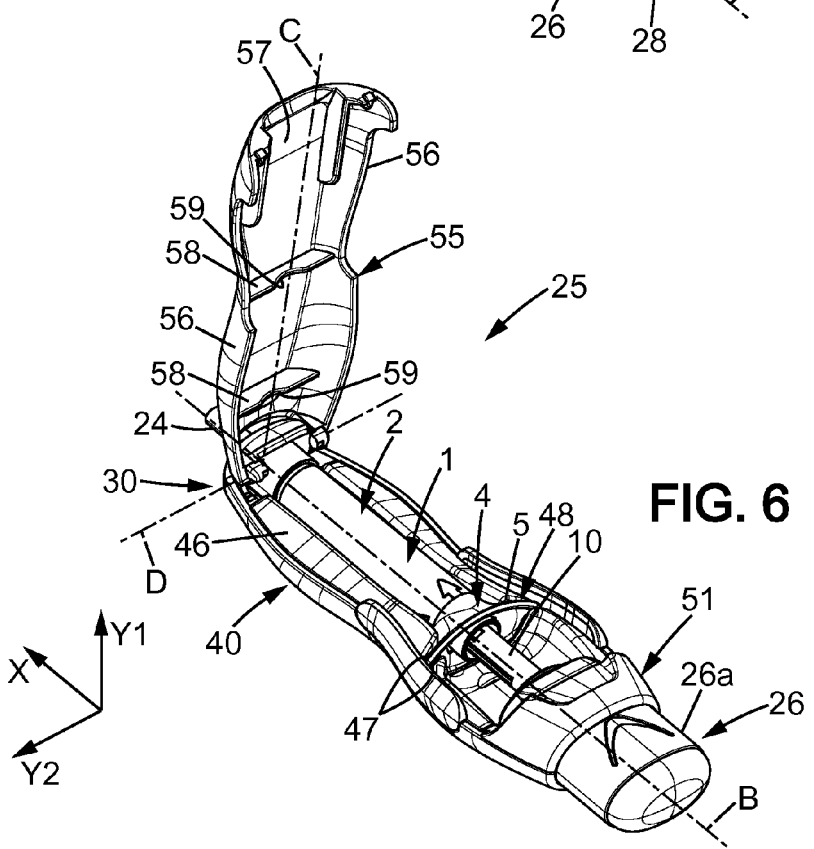
Figure 7:
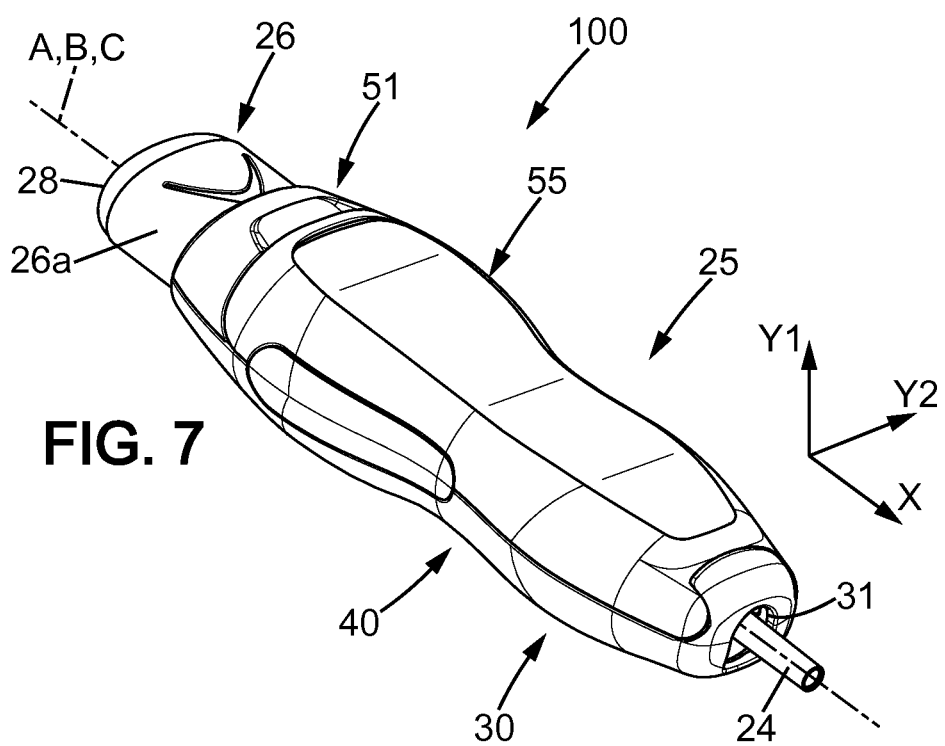

Other objects and advantages of the invention will emerge from the following description of a particular embodiment of the invention given as a non limitative example, the disclosure being made in reference to the enclosed drawings in which:

FIG. 1 is a longitudinal section view of a syringe to be housed in a cover for forming a pen-injector, FIG. 2 is a perspective view from a distal end of a cover for housing the syringe of FIG. 1 according to an embodiment of the invention, the cover comprising a shell adapted to accommodate the syringe and an actuator mounted on the shell to actuate the syringe, FIG. 3 is a perspective view from a proximal end of the cover of FIG. 2, illustrating a lid of the shell in an opened position, angularly spaced from a base of the shell, for the insertion of the syringe in a cavity of the base through a lateral access opening transversally to the base, FIG. 4 is a longitudinal section view of the cover of FIG. 2, illustrating the lid in a closed position and the actuator in a depressed position, FIGS. 5, 6 and 7 are perspective views of steps of a method for forming a pen-injector using the syringe of FIG. 1 and the cover of FIG. 2.

On the Figures, the same reference numbers refer to the same or similar elements.

FIGS. 1 and 2 represent a syringe 1 and a cover 25 that can be assembled as explained in the following of the description to form a pen-injector 100 (shown on FIG. 7) used, in particular by a patient himself, to inject a determined dose of product contained in the syringe 1, especially a therapeutic or pharmaceutical product.

As illustrated on FIG. 1, the syringe 1 comprises:
  a body 2 extending along an axis A between proximal 2a and distal 2b ends and adapted to contain the product to be injected,
  a finger grip 4 protruding outwardly from the body 2,
  a piston rod 10 coaxially mounted in the body 2 so as to slide along the axis A of the body 2, and
  a needle, not shown, mounted on the distal end 2b of the body 2.

Although the invention is not limited thereto, in the illustrated embodiment, the syringe 1 is of the type disclosed in WO 98/39572, namely of dual chamber type.

In particular, the body 2 comprises a tubular sleeve 3 having an upper end 3a to which the finger grip 4 is secured in any appropriate manner, for example through force-fitting and/or snap-fitting. The finger grip 4 comprises two opposite portions, in the form of wings 5, extending perpendicularly to the axis A of the body 2. The piston rod 10 has proximal and distal ends and comprises a first, for example threaded, section 11 that extends from the distal end, and a second, for example straight, section 12 that ends in a push button 13 at the proximal end. The threaded section 11 engages internal threads 6 in the finger grip 4. A cartridge 15 comprising a glass ampoule 16 and having a penetrable stopper 17 at a lower end 15b is arranged within the sleeve 3 resting against an abutment rim 7 at a lower end 3b of the sleeve 3 opposite to the finger grip 4. The cartridge 15 has a lower chamber 18 for a solid preparation and an upper chamber 20 containing a solvent for the lower chamber solid. A lower piston 19 separates the ampoule 16 into lower 18 and upper 20 chambers and a by-pass section 21 controls the solvent overflow to the lower chamber 18. An upper piston 22 closes the upper chamber 20.

The syringe 1 has an initial state, represented on FIG. 1, in which the proximal end of the piston rod 10, comprising the push button 13, is arranged at a first distance from the finger grip 4 corresponding to added lengths of the threaded 11 and straight 12 sections of the piston rod 10. Then, the piston rod 10 can be rotated so that the threaded section 11 advances with respect to the finger grip 4. In doing so, the piston rod 10 advances the upper piston 22 until the lower piston 19 has moved to the bypass 21, the solvent has been forced into the lower chamber 18 and upper 22 and lower 19 pistons have come into contact. At an end-of-stroke of the threaded section 11, the syringe 1 is in a ready-to-be-used state in which the product to be injected has been prepared within the lower chamber 18 and can be injected. In the ready-to-be-used state, the push button 13 of the piston rod 4 is arranged at a second distance, from the finger grip 4, corresponding to the sole length of the straight section 12, the second distance being less than the first distance. By a further straight movement of piston rod 10 along an injection stroke corresponding to the length of the straight section 12, the product may then be ejected through the needle which is inserted through penetrable stopper 17.

As can be seen on FIG. 2, the cover 25 comprises a rigid shell 30 adapted to accommodate the syringe, and an actuator 26 moveably mounted on the shell 30 to actuate the syringe 1.

The shell 30 extends along a longitudinal axis B, parallel to a longitudinal direction X, between proximal 30a and distal 30b ends. The distal end 30b of the shell 30 is provided with a hole 31 arranged along the longitudinal axis A. The shell 30 has a bottom outer surface 32 (visible on FIG. 4) and a top outer surface 34 opposite to each other and spaced apart in a first transverse direction Y1 perpendicular to the longitudinal direction X. Between the bottom 32 and top 34 outer surfaces, the shell 30 has two opposite lateral outer surfaces 33 opposite to each other and spaced apart in a second transverse direction Y2 perpendicular to the longitudinal direction X and the first transverse direction Y1.

The bottom 32, top 34 and lateral 33 outer surfaces of the shell 30 are adapted to ease the grasping and to improve the stability of the shell 30. In particular, in the first transverse direction Y1, the shell 30 is generally flattened. The bottom 32 and top 34 outer surfaces are substantially flat, although these bottom 32 and top 34 outer surfaces may present respectively concave mid-portions 32a, 34a with a slight curvature. The bottom 32 and top 34 outer surfaces define substantially two horizontal plans parallel to each other. Besides, in the second transverse direction Y2, the shell 30 comprises transversally bulged proximal 35 and distal 37 portions connected by a central transversally narrowed portion 36. To that end, each of the lateral outer surfaces 33 has a curvature comprising, from the proximal end 30a to the distal end 30b of the shell 30, a first convexity, a concavity and a second convexity. In the represented embodiment, the lateral outer surfaces 33 are further curved outwardly in the first transverse direction Y1. Two side grips 38, for example made of a soft material, are secured to the lateral outer surfaces 33, at the transversally bulged proximal portion 35.

As can be seen on FIGS. 3 and 4, the shell comprises of two main parts, a base 40 and a lid 55.

The base 40 forms substantially a bottom half of the shell 30 comprising the bottom outer surface 32 and first halves of the lateral outer surfaces 33. In the represented embodiment, as can be seen on FIG. 4, the base 40 comprises an outer housing 41 and an insert 44 secured to the outer housing 41.

The outer housing 41 of substantially U-shaped cross section extends along the longitudinal axis B between the proximal 30a and distal 30b ends of the shell 30. At the distal end 30b, the outer housing 41 has a transverse wall 42 provided with the hole 31. On either sides of the hole 31, two wall portions 43 extending in a lateral plan XY1 are provided respectively with pins protruding outwardly from the wall portions 43 along a same transverse axis.

The insert 44 has a length along the longitudinal axis B between the proximal 30a and distal 30b ends of the shell 30. The insert 44 includes a cavity 45 extending along its length. The cavity 45 is adapted to receive the whole body 2, the finger grip 4 and the whole piston rod 10 of the syringe 1 with the axis A of the body 2 parallel, and in particular coaxial, to the longitudinal axis B of the shell 30. The cavity 45 is formed by a substantially U-shaped recessed portion with respect to a horizontal plane XY2 in which two longitudinal borders 46 extends on either sides of the cavity 45. For the placement of the syringe 1, the insert 44 offers a lateral access opening in the first transverse direction Y1, perpendicularly to the horizontal plane XY2 of the longitudinal borders 46, and extending substantially along its whole length.

In the illustrated embodiment, the insert 44 comprises two pairs of parallel walls 47 extending on either sides of the cavity 45, in the second transverse direction Y2. In particular, each pair of parallel walls 47 includes two walls 47 extending in a transverse plan Y1Y2 and facing each other at a distance suitable for receiving with a friction contact one of the wings 5 of the finger grip 4 of the syringe 1. Each pair of parallel walls 47 thereby defines a slot 48 opened in the first transverse direction Y1 and extending in the second transverse direction Y2 to form a holding member adapted to hold the finger grip 4 of the syringe 1. Between the distal end 30b of the shell 30 and the slots 48, the cavity 45 has a narrower portion adapted to receive the body 2 of the syringe 1, and, between the slots 48 and the proximal end 30a of the shell 30, the cavity 45 has a widened portion adapted to receive the push button 13 of the syringe 1 and a part of the actuator 26 so as to allow their movement along the longitudinal direction X.

As can be seen on FIG. 4, the insert 44 also has a friction member, in the form of a tab 49, extending in the longitudinal direction X. The tab 49 is shaped, in particular through a curvature, to have an inner surface slightly offset in the first transverse direction Y1 with respect to the cavity 45, and to be resiliently deformable.

At the proximal end 30a of the shell 30, a piece 50 of inverted U-shaped cross section is secured to the outer housing 41 to form a hoop 51 on the base 40 arranged coaxially to the longitudinal axis A. The hoop 51 delimits an opening arranged along the longitudinal axis B and adapted to receive the actuator 26.

The actuator 26 is substantially cylindrical along an axis, of elliptic cross section in the represented embodiment. The actuator 26 has an outer surface 26a, an end provided with a flat actuating surface 27 and an opposite end provided with a grip 28, for example made of a soft material. The actuator 26 also has a stop 29 protruding outwardly from the outer surface 26a close to the actuating surface 27. The actuator 26 is mounted on the proximal end 30a of the shell 30, through the opening of the hoop 51, with its axis arranged coaxial to the longitudinal axis B, the tab 49 being resiliently biased against the outer surface 26a of the actuator 26. The actuating surface 27 is arranged within the cavity 45 of the base 40 so as to move the piston rod 10 when the syringe 1 is placed in the shell 30 and the actuator 26 is pressed as explained below, whereas the opposite end with the grip 28 protrudes outwardly from the shell 30.

The actuator 26 is mounted on the shell 30 so as to slide along the longitudinal axis B of the shell 30. Therefore, the actuator 26 in an extended position, shown on FIG. 3, in which the actuating surface 27 is spaced apart from the distal end 30b of the shell 30 of a maximum distance, may be moved in translation along the longitudinal axis B to a depressed position, shown on FIG. 4, in which the actuating surface 27 is spaced apart from the distal end 30b of the shell 30 of a minimum distance, through an action in the longitudinal direction X exerted on the grip 28 of the actuator 26 by the patient. The extended position and the depressed position are spaced apart of a distance greater than or equal to the injection stroke of the piston rod 10 which is, in the illustrated embodiment, the length of the straight portion 12. Besides, to make sure that, upon actuation, the required dose of product will be injected to the patient, the actuating surface 27 of the actuator 26 in the extended position is arranged at a distance from the slots 48 of the holding member corresponding to the second distance between the push button 13 and the finger grip 4 of the syringe 1 in the ready-to-be-used state.

It should be noted that, although the invention has been described with an actuator 26 slidably mounted on the proximal end 30a of the shell 30, any other arrangement of the actuator 26 on any other part of the shell 30 could be provided.

The lid 55 forms substantially a top half of the shell 30 comprising the top outer surface 34 and second halves of the lateral outer surfaces 33. The lid 55 of substantially U-shaped cross section extends along an axis C between proximal 55a and distal 55c ends. In particular, the lid 55 comprises two lateral walls 56, along the axis C, facing each other and bearing respectively the second halves of the lateral outer surfaces 33, and a top wall 57, along the axis, between the lateral walls 56 and bearing the top outer surface 34. The lid 55 also comprises two transverse walls 58, perpendicular to the axis C and provided each with an indentation 59 for maintaining the body 2 of the syringe 1. At the distal end 55b, the lateral walls 56 of the lid 55 have recesses arranged to receive the pins of the outer housing 41 of the base 40. The recesses and the pins thereby define a pivot joint around a transverse pivot axis D by means of which the lid 55 is pivotally mounted on the base 40.

In particular, as shown on FIGS. 2 and 4, the lid 55 has a closed position in which it covers the cavity 45, the axis C of the lid 55 being parallel to the longitudinal axis B of the shell 30, free edges of the lateral walls 56 of the lid 55 resting on the longitudinal borders 46 of the base 40 and the proximal end 55a of the lid 55 being adjacent to the hoop 51. The lid 55 is movably attached to the base 40 and can be pivoted around the pivot axis D in an opened position, shown in FIG. 3. In the opened position, the lid 55 extends substantially in the first transverse direction Y1 at the distal end 30b of the shell 30 so as to be angularly spaced from the base 40 and to allow the insertion of the syringe 1 within the cavity 45 transversally through the lateral access or the removal of the syringe 1 from the cavity 45 transversally through the lateral access.

In relation with FIGS. 5, 6 and 7, a method for forming a pen-injector 100 using the syringe 1 of FIG. 1 and the cover 25 of FIG. 2 is disclosed.

On FIG. 5, the lid 55 of the shell 30 is in the opened position and the syringe 1 can be placed within the cavity 45 of the base 40 through the lateral access. In particular, the syringe 1 is brought close to the cavity 45 substantially along the first transverse direction Y1 with respect to the base 40 and slightly tilted to place the lower end of the body 2 within the cavity 45 through the lateral access and to insert the needle of the syringe 1 covered by a protective cap 24 in the hole 31 of the base 40.

On FIG. 6, to complete the placement of the syringe 1 within the cavity 45, the syringe 1 is moved from the initial state to the ready-to-be-used state. Of course, the syringe 1 could have been moved to the ready-to-be-used at an earlier step. The body 2 of the syringe 1 can then be moved, through a rotation movement, along the first transverse direction Y1, so that the syringe 1 lays within the cavity 45 of the base 40 with the axis A of the body 2 parallel to the longitudinal axis B of the shell 30 and the wings 5 of the finger grip 4 held in the slots 48 of the holding member.

On FIG. 7, the lid 55 is shut down on the base 40 to cover the cavity 45 and the syringe 1 received therein, the indentations 59 of the lid 55 coming into contact with the body 2 of the syringe 1.

The pen-injector 100 is formed, the syringe 1 being coaxially arranged within the shell 30, the shell 30 surrounding the body 2 and the piston rod 10 of the syringe 1, only a part of the needle extending out through the distal end 30b of the shell 30.

What is claimed is:

1. Cover (25) for housing a syringe (1) and thereby forming a pen-injector, said syringe (1) comprising a body (2) extending along an axis (A) between proximal (2a) and distal (2b) ends and adapted to contain a product to be injected, a finger grip (4) protruding outwardly from the body (2), a piston rod (10) coaxially mounted in the body (2) so as to slide along the axis (A) of the body (2), and a needle mounted on the distal end (2b) of the body (2), said cover (25) consisting of:
   a shell (30) extending along a longitudinal axis (B) between proximal (30a) and distal (30b) ends, said shell (30) being adapted to accommodate the body (2), the finger grip (4) and the piston rod (10) of the syringe (1) so that at least a part of the needle of the syringe (1) extends through the distal end (30b) of the shell (30),
   an actuator (26) moveably mounted on the shell (30) and arranged to actuate the piston rod (10) of the syringe (1) when the syringe (1) is placed in the shell (30), said cover (25) being characterised in that the shell (30) is provided with a holding member (48) adapted to hold the finger grip (4) of the syringe (1), and in that the shell (30) comprises a base (40) and a lid (55), said base (40) including a cavity (45) extending along the longitudinal axis (B) of the shell (30) and adapted to receive the syringe (1) with the axis (A) of the body (2) parallel to the longitudinal axis (B) of the shell (30), said lid (55) being movable with respect to the base (40) between an opened position in which the shell (30) presents a lateral access to the cavity (45) to allow insertion or removal of the syringe (1), and a closed position, and in that the actuator (26) is movably mounted on the shell (30) between an extended position, wherein it protrudes from the shell, and a depressed position.

2. Cover (25) according to claim 1, wherein the lid (55) is pivotally mounted on the base (40) about a pivot axis (D) between the opened position in which said lid (55) is angularly spaced from the base (40), and the closed position in which said lid (55) covers the cavity (45).

3. Cover (25) according to claim 2, wherein the lid (55) is mounted on the base (40) at the distal end (30b) of the shell (30) and the pivot axis (D) extends transversally with respect to the longitudinal axis (B) of the shell (30).

4. Cover (25) according to claim 1, wherein the holding member comprises two slots (48) opened transversally with respect to the longitudinal axis (B) of the shell (30) and extending on either sides of the cavity (45), said slots (48)

being designed to accommodate two opposite portions (5) of the finger grip (4) projecting transversally from the body (2).

5. Cover (25) according to claim 1, wherein the base (40) has a hoop (51) at the proximal end (30a) of the shell (30), said hoop (51) being arranged coaxially to the longitudinal axis (B) of the shell (30) and delimiting an opening in which the actuator (26) is mounted so as to slide along the longitudinal axis (B) of the shell (30).

6. Cover (25) according to claim 5, wherein the actuator (26) has an outer surface (26a) and the base (40) comprises a friction member (49) resiliently biased against the outer surface (26a) of the actuator (26).

7. Cover (25) according to claim 1, wherein the shell (30) has two opposite outer surfaces (32, 34) which are substantially flat.

* * * * *